United States Patent
Sauter et al.

(10) Patent No.: US 6,664,421 B2
(45) Date of Patent: Dec. 16, 2003

(54) PROCESS FOR PREPARING ZOLPIDEM

(75) Inventors: Markus Sauter, Gensingen (DE); Wolfgang Wohlleben, Hueffelsheim (DE)

(73) Assignee: Boehringer Ingelheim Pharma KG, Ingelheim (DE)

(*) Notice: Subject to any disclaimer, the term of this patent is extended or adjusted under 35 U.S.C. 154(b) by 0 days.

(21) Appl. No.: 10/446,434

(22) Filed: May 27, 2003

(65) Prior Publication Data

US 2003/0195375 A1 Oct. 16, 2003

Related U.S. Application Data

(62) Division of application No. 10/318,900, filed on Dec. 13, 2002, now Pat. No. 6,583,285, which is a continuation of application No. 10/133,830, filed on Apr. 26, 2002, now abandoned.

(60) Provisional application No. 60/290,747, filed on May 14, 2001.

(30) Foreign Application Priority Data

May 3, 2001 (DE) .......................... 101 21 638

(51) Int. Cl.$^7$ .............................. C07C 233/65
(52) U.S. Cl. ....................................... 564/169
(58) Field of Search .......................... 564/169

(56) References Cited

FOREIGN PATENT DOCUMENTS

EP    0 251 859 B1    11/1990

OTHER PUBLICATIONS

Trapani, et al; "Novel 2–Phenylimidazo[1,2–alpha]pyridine Derivatives as Potent and Selective Ligands for Peripheral Benzodiazepine Receptors: Synthesis, Binding Affinity, and in Vivo Studies"; J. Med. Chem. 1999, 42(19), pp. 3934–3941.

Trapani, et al; "Synthesis and Binding Affinity of 2–Phenylimidazo[1,2–alpha]pyridine Derivatives for both Central and Peripheral Benzodiazephine Receptors. A New Series of High–Affinity and Selective Ligands for the Peripheral Type"; J. Med. Chem. 1997, 40(19), pp. 3109–3118.

*Primary Examiner*—Patricia L. Morris
(74) *Attorney, Agent, or Firm*—Robert P. Raymond; Alan R. Stempel; Michael P. Morris

(57) ABSTRACT

The invention relates to a process for preparing a compound of formula (I)

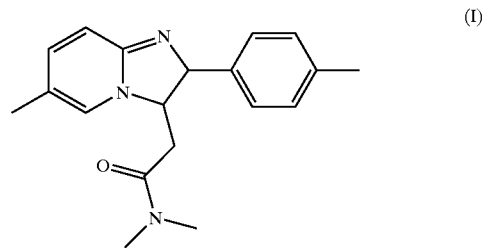

wherein
a compound of formula (II),

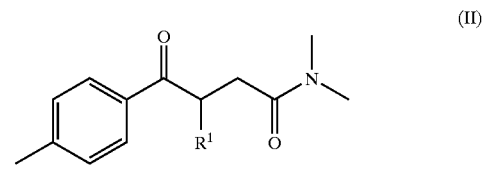

wherein
$R^1$ denotes chlorine, bromine, iodine, —O—COCH$_3$, tosylate or mesylate, is reacted with a compound of formula (III),

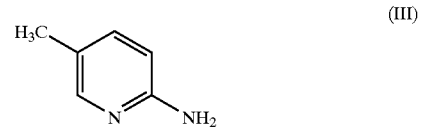

optionally in a suitable diluent and/or in the presence of a suitable added reagent or catalyst, the reaction being carried out in a temperature range from 20 to 80° C.

1 Claim, No Drawings

PROCESS FOR PREPARING ZOLPIDEM

RELATED APPLICATIONS

This application is a division of U.S. Ser. No. 10/318,900 filed Dec. 13, 2002, now U.S. Pat. No. 6,583,285, which is a continuation of U.S. Ser. No. 10/133,830, filed on Apr. 26, 2002, now abandoned which claims benefit of U.S. Provisional Application Serial No. 60/290,747, filed on May 14, 2001 is hereby claimed.

FIELD OF THE INVENTION

The invention relates to a process for preparing zolpidem.

BACKGROUND OF THE INVENTION

Zolpidem is a known sedative which has the following structure:

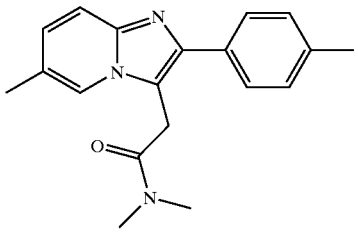

EP 0 251 859 describes a process for preparing zolpidem. The six-step synthesis starting with a bromoacetophenone is a generally laborious method.

A process for preparing compounds analogous to zolpidem in which 2-aminopyridines and corresponding bromoketoamides are reacted is described in the literature (J. of Med. Chem., 1999, Vol. 42, No. 19,3934–3941).

The problem of the present invention is therefore to provide an improved, economical process for preparing zolpidem which can be used on an industrial scale.

DETAILED DESCRIPTION OF THE INVENTION

The present invention solves the problem outlined above by the method of synthesis described hereinafter.

The invention thus relates to a process for preparing a compound of formula (I)

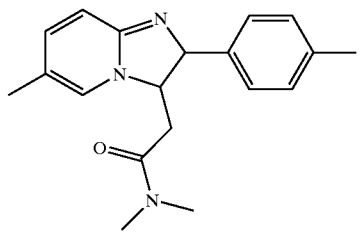

wherein a compound of formula (II)

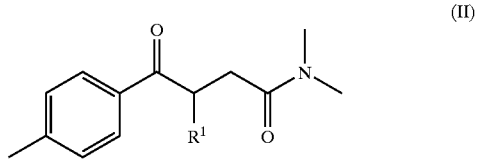

wherein $R^1$ denotes chlorine, bromine, iodine, —O—COCH$_3$, tosylate or mesylate, is reacted with a compound of formula (III),

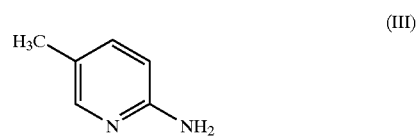

optionally in a suitable diluent and/or in the presence of a suitable added reagent or catalyst, characterised in that the reaction is carried out in a temperature range from 20 to 80° C.

In a particularly preferred process a diluent is used which is selected from among acetonitrile, N-methylpyrrolidinone, tetrahydrofuran, acetone, ethanol and dichloromethane.

In another preferred process, acetonitrile is used as the diluent.

According to the invention, a process in which the reaction is carried out at a temperature of about 60 to 75° C., preferably 70° C., is particularly important.

Also preferred is a process in which the compound of formula (II) is used in a molar ratio of 1:1 to 1:3 to the compound of formula (III).

Particularly preferred is a process in which the compound of formula (II) is used in a molar ratio of about 1:1.3 to the compound of formula (III).

Most particularly preferred is a process in which an added reagent and/or catalyst is used which is selected from among p-toluenesulphonic acid monohydrate, sodium hydrogen carbonate, sodium acetate, pyridine, dimethylaminopyridine, magnesium sulphate, triethylamine, trimethylorthoformate and tetrabutylammonium bromide.

The invention further relates to the compound of formula (II)

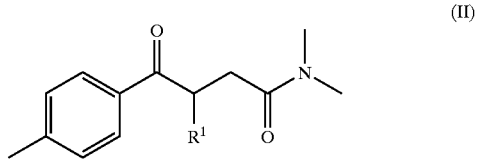

wherein $R^1$ denotes bromine.

The present invention also relates to a process for preparing a compound of formula (II), herein a compound of formula (IV)

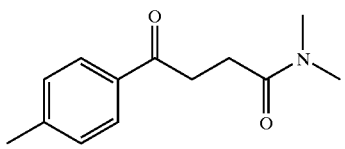
(IV)

is reacted with elemental bromine in a diluent, preferably dichloromethane.

The reaction of a compound of formula (IV) with elemental bromine is generally carried out at a temperature of 10 to 50° C., preferably 15 to 35° C., more preferably 18 to 30° C., most preferably about 20 or 25° C.

The compound of formula IV is generally used in a molar ratio of 1.5:1 to 1:1.5, preferably about 1:1.2, to elemental bromine.

The invention also relates to the use of compounds of formula (II) for preparing pharmaceutically active compounds.

Preferably, the compound of formula (II) is used to prepare zolpidem.

The invention further relates to a process for preparing a compound of formula (I), this process comprising the following steps:

a) reacting the compound of formula (IV) in an organic diluent at a temperature of 30 to 50° C., preferably about 40° C., with elemental bromine.

b) washing the reaction mixture with water, c) after phase separation, concentrating the organic phase by evaporation and optionally diluting it with another organic diluent, and d) reacting the concentrated organic phase of a) to c) with the compound of formula (III) at 20 to 80° C., preferably 60 to 75° C., preferably about 70° C., without isolating the intermediate product.

The present invention further relates to the use of the compound of formula (I) for preparing the pharmaceutically acceptable salts thereof.

The compound of formula (I) is preferably used to prepare zolpidem semitartrate.

Acids suitable for forming a salt of the compounds according to the invention include, for example, hydrochloric acid, hydrobromic acid, sulphuric acid, phosphoric acid, nitric acid, oxalic acid, malonic acid, fumaric acid, maleic acid, tartaric acid, citric acid, ascorbic acid and methanesulphonic acid, particularly tartaric acid.

In a preferred embodiment of the process according to the invention for preparing the compound of formula II, one equivalent of the compound of formula IV is dissolved in a diluent, preferably glacial acetic acid, ethyl acetate, n-butyl acetate or diethylether, most preferably ethyl acetate. A solution of usually 1 to 1.5 equivalents, preferably one equivalent, of bromine is added dropwise in a diluent, preferably ethyl acetate, at a temperature of 40 to 70° C., preferably about 45° C., and stirred for 2 to 24 h, preferably to 15 h, most preferably 12 h, at a temperature of 10 to 50° C., preferably 15 to 35° C., more preferably 18 to 30° C., most preferably about 20 or 25° C. The suspension obtained is filtered, the residue is added to a little water and stirred for about 0.5 to 2 h, preferably about 1 h. The suspension is filtered again and the residue is washed with water. The crystals obtained are dried, preferably in a vacuum drying cupboard at 40 to 80° C., preferably at about 70° C.

In a preferred embodiment of the process according to the invention for preparing the compound of formula I, about 1 equivalent of the compound of formula (II) is placed in a diluent, for example acetonitrile, and a solution of generally 2 equivalents of the compound of general formula (III) and a diluent, for example acetonitrile, is added dropwise at 20 to 80° C., more preferably at 40 to 75° C., most preferably at a temperature of about 70° C. within 0.5 to 3 h, preferably 1 to 2 h, more preferably about 1.5 or 1.75 h. After it has all been added, the mixture is stirred for 2 to 6 h, preferably 2 to 5 h, more preferably about 2.5 to 3 h.

The reaction mixture is then diluted with a diluent, preferably dichloromethane, and washed one to five times, preferably three times, with water. The organic phase is extracted one to five times with hydrochloric acid, preferably 2 N hydrochloric acid. The combined acid phases are adjusted to a pH of between about 7 and 9, preferably to a pH of about 8, using a base, preferably sodium hydroxide solution, more preferably 20% sodium hydroxide solution. After the reaction mixture has been cooled it is extracted one to five times with an organic diluent, selected from among dichloromethane, toluene, ethyl acetate, n-butyl acetate and methyl-tert.-butylether, preferably dichloromethane and ethyl acetate, more preferably ethyl acetate. The combined organic phases are dried, preferably with magnesium sulphate, and concentrated by evaporation. The product which crystallises out is mixed with a little water and stirred for 5 to 20 h, preferably 15 h, and the crystals are filtered off, washed with water and dried, preferably at 30 to 80° C., preferably at 60° C., for 1 to 10 h, preferably 5 h.

In a preferred embodiment of the process according to the invention for preparing the semitartrate salt of the compound of general formula I, generally 2 equivalents of the compound of formula I are placed in a diluent, preferably methanol, ethyl acetate, Isopropanol or ethanol, more preferably methanol, and a solution of 1 equivalent of (2R, 3R)-(+)-tartaric acid in a diluent, preferably methanol, ethanol or isopropanol, more preferably methanol, is added.

A precipitation agent, preferably tert.butylmethylether, an isopropanol/methanol-mixture or a methanol/ether mixture, preferably tert.butylmethylether, is optionally added. The mixture is stirred for 1 to 24 h, preferably 12 h, at a temperature of 15 to 30° C., preferably at about 20 or 25° C. The suspension formed is stirred for a further 0.5 to 3 h, preferably about 1 hour at a temperature of 0 to 20° C., preferably 3 to 10° C., most preferably at about 5° C. The crystals obtained are filtered, optionally washed with a solvent, preferably with tert.butylmethylether, and the crystals are dried, preferably for 1 to 10 h, more preferably for 5 hours at a temperature of 20 to 70° C., preferably about 50° C.

In a particularly preferred embodiment of the process according to the invention, about 1 equivalent of the compound of formula (IV) is placed in a diluent, for example ethyl acetate, butyl acetate or dichloromethane, preferably dichloromethane, and heated to 30 to 50° C., preferably 40° C. Preferably, catalytic amounts, preferably 5 to 6 mol-%, of HBr are added to the reaction mixture. Then 1.2 equivalents of bromine are added dropwise. The reaction mixture is stirred for another 60 min, preferably 30. min. The mixture is cooled to about 20 to 25° C. and extracted with water. The organic phase is evaporated down to about 10% (v/v) and then diluted with another diluent, preferably tetrahydrofuran, N-methylpyrrolidinone or acetonitrile, preferably acetonitrile. The mixture is added dropwise to a solution of 1.3 equivalents of 6-amino-3-picoline and a diluent, preferably tetrahydrofuran, N-methylpyrrolidinone or acetonitrile, preferably acetonitrile. The resulting mixture is then stirred for about 2 h at 50 to 80° C., preferably 70° C. The reaction mixture is combined with an organic diluent, preferably toluene, extracted with an aqueous solution, for example 2N hydrochloric acid, and the organic phase is discarded. The aqueous phase is again mixed with an organic diluent, adjusted to a pH of about 4, and the organic phase is discarded again. The extraction step is repeated at a pH of about 8 to 9. After the aqueous phase has been separated off the organic phase is evaporated down to about 10%. The residue is combined with diisopropylether, diethylether or methyl-tert.butylether, preferably methyl-tert.butylether, and stirred for about 30 to 60 minutes at about 0 to 15° C., preferably 5° C. The crystals formed are washed and dried.

The procedure according to the invention leads to an economical process with a high space-time yield with regard to the compound of formula I or the pharmacologically acceptable salts thereof and a high yield and purity of the intermediate product of formula II, which can be further processed without being isolated or purified by chromatography.

The Examples that follow serve to illustrate the processes for preparing the compound of formula I. carried out by way of example. They are to be understood as examples of possible procedures without restricting the invention to their contents.

EXAMPLE 1

3-(4-methyl-benzoyl)-2-bromo-propyl-dimethylamide 18.6 g (84.8 mmol) of 3-(4-methyl-benzoyl)-propyl-dimethylamide are dissolved in 50 ml of glacial acetic acid. A solution of 13.55 g (84.8 mmol) of bromine and 45 ml of glacial acetic acid is added dropwise within 50 minutes at ambient temperature and the mixture is then stirred overnight. The suspension formed is filtered and washed with 30 ml of glacial acetic acid. The filter residue is added to 200 ml of distilled water, triturated thoroughly and stirred for 1 hour. The product is filtered again and washed with another 200 ml of water. The crystals obtained (21.16 g) are dried for 6 hours in a vacuum drying cupboard at 70° C.

Yield 18.18 g of white crystals (71.9% of theory)

Melting point: 119–121° C.

EXAMPLE 2

N,N-6-Trimethyl-2-(4-methylphenyl)imidazo[1,2-a] pyridine-3-acetamide 50 g (167.7 mmol) of 3-(4-methyl-benzoyl)-2-bromo-propyl-dimethylamide are placed in 500 ml of acetonitrile. A solution of 36.27 g (335.4 mmol) of 6-amino-3-picoline and 350 ml of acetonitrile is added dropwise at 60° C. within 1.75 hours and once the solution has all been added the mixture is stirred for another 4 hours. The resulting solution is diluted with 1000 ml of dichloromethane and washed three times with 2000 ml of distilled water. Then the organic phase is extracted three times with 1000 ml of 2N hydrochloric acid. The combined acid phases are adjusted to pH 8 with 20% sodium hydroxide solution and, after being cooled, extracted three times with 1 liter of dichloromethane. These organic phases are combined, dried with magnesium sulphate and concentrated by evaporation. The crystals obtained are triturated with 500 ml of distilled water, stirred overnight, filtered off, washed again with 50 ml of distilled water and the residue is dried in a vacuum drying cupboard for 5 hours at 60° C.

Yield: 17.94 g of light-brown crystals (45.7% of theoretical).

EXAMPLE 3

N,N-6-Trimethyl-2-(4-methylphenyl)imidazo[1,2-a] pyridine-3-acetamide 10.0 g (33.5 mmol) of 3-(4-methyl-benzoyl)-2-bromo-propyl-dimethylamide and 7.25 g (67.0 mmol) of 6-amino-3-picoline are dissolved in 170 ml of 1,3-dimethyl-2-imidazolidinone and stirred for 3 hours at 60° C. The reaction mixture is cooled and diluted with 100 ml of dichloromethane. It is then washed five times with 150 ml of distilled water. The organic phase is washed twice with 150 ml of 2N hydrochloric acid. The combined acid phases are adjusted to pH 8 with 2N sodium hydroxide solution. The mixture is extracted twice with 150 ml of dichloromethane, the organic phases are dried with $MgSO_4$ and concentrated by evaporation. The brown oil obtained is mixed with 50 ml of n-heptane and stirred for 30 minutes. The supernatant diluent is decanted off from the precipitated product which is then washed twice with 10 ml of n-heptane. The residue is evaporated down again, combined with 200 ml of distilled water and stirred for 30 minutes. The product is filtered off, washed with 50 ml of distilled water and dried.

Yield: 2.38 g of beige crystals (23.1% of theoretical.)

Melting point: 194–195° C.

EXAMPLE 4

N,N-6-Trimethyl-2-(4-methylphenyl)imidazo[1,2-a] pyridine-3-acetamide semitartrate 17.94 g (94%) (54.9 mmol) of N,N-trimethyl-2-(4-methylphenyl)imidazo[1,2-a]pyridine-3-acetamide are placed in 90 ml of methanol. A solution of 4.13 g (27.5 mmol) of (2R, 3R)-(+)-tartaric acid and 125 ml of methanol are added, followed by 28 ml of methyl-tert.-butyl-ether (MTBE) within 30 seconds. The mixture is stirred for 15 h at ambient temperature. The light-brown suspension formed is stirred for another 1 hour at 5° C., filtered off, the residue is washed with 50 ml of MTBE, and the crystals are dried for 5 hours in a vacuum drying cupboard at 50° C.

Yield: 18.3 g crystals (87.2% of theoretical.)

EXAMPLE 5

N,N-6-Trimethyl-2-(4-methylphenyl)imidazo[1,2-a] pyridine-3-acetamide 100 g (0.456 mol) of 3-(4-methyl-benzoyl)-propyl-dimethylamide are dissolved in 400 ml of dichloromethane.

2 g (0.025 mol) of hydrogen bromide are piped into the solution which is then refluxed. Then 86.1 g (0.539 mol) of bromine is added dropwise within 45 minutes and the mixture is stirred for 30 min. It is then cooled to ambient temperature and washed with 600 ml of distilled water. The aqueous phase is discarded. The organic phase is evaporated down to about 10% (v/v) and then diluted with 300 ml of acetonitrile. This solution is added dropwise within 45 min to a solution of 66.62 g (0.616 mol) of 6-amino-3-picoline in 150 ml of acetonitrile at 70° C. and stirred for 1.5 h. Then 400 ml of toluene are added at 20–30° C. and the mixture is then extracted with 500 ml of 2N hydrochloric acid. The toluene phase is discarded, the aqueous phase is again combined with 400 ml of toluene and adjusted to pH 4 with 20% sodium hydroxide solution. The toluene phase is discarded, the aqueous phase is combined with 400 ml of toluene and adjusted to pH 8.5 with 20% sodium hydroxide solution. The toluene phase is separated off and evaporated down to 10% (v/v). The residue is combined with MTBE and stirred for 2 h at 5° C. The crystals obtained are suction filtered, washed with MTBE and dried.

Yield: 43 g of zolpidem (30.7%).

What is claimed is:

1. The compound of formula (II)

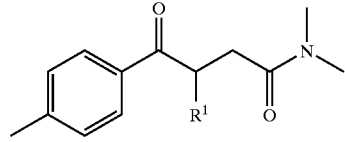

(II)

wherein $R^1$ denotes bromine.

* * * * *